United States Patent [19]

Schoolman

[11] Patent Number: 5,493,595
[45] Date of Patent: Feb. 20, 1996

[54] STEREOSCOPICALLY DISPLAYED THREE DIMENSIONAL MEDICAL IMAGING

[75] Inventor: Arnold Schoolman, Kansas City, Mo.

[73] Assignee: Schoolman Scientific Corp., Kansas City, Mo.

[21] Appl. No.: 253,424

[22] Filed: Jun. 2, 1994

Related U.S. Application Data

[63] Continuation of Ser. No. 91,461, Jul. 14, 1993, abandoned, which is a continuation of Ser. No. 615,218, Nov. 19, 1990, abandoned, which is a continuation-in-part of Ser. No. 229,472, Aug. 8, 1988, abandoned, which is a continuation-in-part of Ser. No. 179,059, Apr. 8, 1988, abandoned, which is a continuation-in-part of Ser. No. 935,066, Nov. 21, 1986, Pat. No. 4,737,972, which is a continuation-in-part of Ser. No. 671,436, Nov. 14, 1984, abandoned, which is a continuation-in-part of Ser. No. 616,385, Jun. 1, 1984, Pat. No. 4,559,555, which is a continuation-in-part of Ser. No. 351,917, Feb. 24, 1982, abandoned.

[51] Int. Cl.⁶ .......................... G03C 9/08; G06F 159/00
[52] U.S. Cl. .................................. 378/41; 128/653.1
[58] Field of Search .................. 364/413.26, 413.25, 364/413.24, 413.22, 413.14, 413.13, 413.19; 378/23, 41, 42, 98.6, 137; 395/119; 250/363.04, 369; 128/653.1

[56] References Cited

U.S. PATENT DOCUMENTS

| | | | |
|---|---|---|---|
| 3,705,261 | 12/1972 | Langley | 348/42 |
| 3,783,282 | 1/1974 | Hoppenstein | 378/41 |
| 3,840,747 | 10/1974 | Macovski | 250/369 |
| 3,873,834 | 3/1975 | Dammann et al. | 378/23 |
| 3,949,229 | 4/1976 | Albert | 378/98.6 |
| 4,052,888 | 10/1977 | Brown et al. | 73/625 |
| 4,057,745 | 11/1977 | Albert | 378/137 |
| 4,214,267 | 7/1980 | Roese et al. | 378/42 |
| 4,310,849 | 1/1982 | Glass | 358/88 |
| 4,521,688 | 6/1985 | Yin | 250/363.04 |
| 4,559,555 | 12/1985 | Schoolman | 358/88 |
| 4,672,649 | 6/1987 | Rutt | 378/10 |
| 4,692,878 | 9/1987 | Ciongoli | 395/119 |
| 4,710,002 | 12/1987 | Pomerantzeff | 351/205 |
| 4,798,210 | 1/1989 | Ledley | 128/600.1 |
| 4,845,626 | 7/1989 | Ohhashi | 364/413.16 |

FOREIGN PATENT DOCUMENTS

| | | |
|---|---|---|
| 61-80457 | 4/1986 | Japan . |
| 0080457 | 8/1986 | Japan . |

Primary Examiner—Gail O. Hayes
Assistant Examiner—Joseph Thomas
Attorney, Agent, or Firm—Litman, McMahon and Brown

[57] ABSTRACT

A stereoscopically displayed three dimensional medical imaging system derives image data from a tomographic imaging apparatus and reconstructs the image data into a three dimensional model and displays right and left stereoscopic three dimensional image components of the model on corresponding right and left video display devices of a stereoscopic viewing unit. The system includes a system computer interfaced to the imaging apparatus and a pair of image channels, each including a three dimensional display processor, and a video display device. The three dimensional display processors receive polygon image data, reconstruct it into a three dimensional form, and select image data representing a three dimensional view from a selected perspective. The system computer generates the polygon image data and controls the display processors to present mutually angularly displaced views of the same three dimensional image to form the stereoscopic image components.

36 Claims, 7 Drawing Sheets

STEREOSCOPICALLY DISPLAYED THREE DIMENSIONAL MEDICAL IMAGING

CROSS-REFERENCE TO RELATED APPLICATIONS

The present application is a continuation of Ser. No. 08/091,461, filed Jul. 14, 1993, abandoned, which is a continuation of Ser. No. 07/615,218, filed Nov. 19, 1990, abandoned, which is a continuation-in-part of Ser. No. 07/229,472 filed Aug. 8, 1988 for STEREOSCOPICALLY DISPLAYED THREE DIMENSIONAL MEDICAL IMAGING which is a continuation-in-part of Ser. No. 07/179,059 filed Apr. 8, 1988 for HIGH FIDELITY STEREOSCOPIC COMBINED LCD AND CRT TELEVISION DISPLAY, which is a continuation-in-part of Ser. No. 06/935,066 filed Nov. 21, 1986 for STEREOSCOPIC FLUOROSCOPE ARRANGEMENT, now U.S. Pat. No. 4,737,972, which is a continuation-in-part of Ser. No. 06/671,436 filed Nov. 14, 1984, abandoned, which is a continuation-in-part of Ser. No. 06/616,385 filed Jun. 1, 1984 for STEREOSCOPIC REMOTE VIEWING SYSTEM, now U.S. Pat. No. 4,559,555, which is a continuation-in-part of Ser. No. 06/351,917 filed Feb. 24, 1982 for PORTABLE REMOTE TERMINAL WITH HEAD HELD DISPLAY, abandoned, all such applications being incorporated herein by reference.

FIELD OF THE INVENTION

The present invention relates to improved medical image display methods and apparatus and, more particularly, to methods and apparatus for stereoscopically displaying three dimensional medical image data.

BACKGROUND OF THE INVENTION

Physicians have an important need for knowledge and information of the structure and condition of a patient's internal anatomy. More importantly, physicians have a need for such information which is obtained by non-invasive techniques. These needs were first addressed by the use of x-rays. In recent years, however, the x-ray machine has been supplemented in many situations by medical imaging techniques which yield three dimensional (3D) information. These techniques include, for example, computed tomography, magnetic resonance imaging, positron emission tomography, tomographic gamma scintillation imaging, and ultrasonic scanning.

Perhaps the best known technique of this type is computed tomography (CT), also known as computed axial tomography (CAT). With computed tomography, a complete three dimensional examination is made up of a sequence of two dimentional (2D) cross sections or "slices". Slice information is acquired by rotating a thin, fan shaped beam of x-rays about the long axis of the patient. Each slice is irradiated by its edges; the transmitted x-ray beams are captured with position sensitive radiation detectors and, thus, x-ray attenuation measurements are obtained from many different directions across the slice. The two dimensional images are reconstructed from these measurements by a mathematical procedure known as convolution and back projection. The output of the reconstruction procedure is an array of numbers (known as pixels in 2D, or voxels in 3D) representing the radiological density (x-ray attenuation) at points within the slice.

A recently developed imaging modality which does not employ x-rays is magnetic resonance imaging (MRI). This technique uses large magnetic fields to excite protons within the body through the phenomenon of nuclear magnetic resonance (NMR). The excited protons produce a radio frequency (RF) signal which can be position encoded. Three dimensional information can be built up slice by slice, as with x-ray CT. The two dimensional slices are reconstructed for viewing using mathematical procedures analogous to those used in x-ray CT. In MRI, the information associated with each voxel is a composite of proton density (essentially, the amount of water present) and so called T1 and T2 relaxation times, which are functions of physical and chemical structure.

Other three dimensional imaging techniques fall within the realm of nuclear medicine. The basic principle here is to introduce radioactive substances (radio pharmaceuticals) into the body, relying on their pharmacological properties for uptake into specific organs (for example, radioactive iodine can be used to label the thyroid). These radioactive substances produce radiation which may be measured with position sensitive detectors external to the body, known as gamma cameras. Two dimensional projected images (comparable to those obtained with conventional x-rays) can be generated with analog electronic circuitry. To obtain reliable three dimensional information, however, single photon emission computed tomography (SPECT) or positron emission tomography (PET) is employed, both of which rely on digital techniques. SPECT systems make use of routine gamma radiation emitting radiopharmaceuticals combined with tomographic scanning techniques and may be thought of as a tomographic gamma scintillation imaging technique. PET systems, in contrast, employ annihilation coincidence detection to detect positron annihilation radiation from positron emitting radiopharmaceuticals. In both of these modalities, the information associated with each voxel is a measure of the concentration of radiopharmaceutical at the corresponding volume increment within the patient. SPECT and PET differ from CT and MRI in that the images are fundamentally physiological rather than anatomical (although certain MRI studies have a physiological component). Thus, for example, nuclear medicine studies are used to demonstrate abnormal growth activity in bones which otherwise appear normal.

Another common imaging modality which yields three dimensional information in digital format is diagnostic ultrasound. This technique relies on the reflection of sound waves at interfaces within the body (e.g., between fluid and soft tissue) to generate echoes; the elapsed time between the transmission of a pulsed sound wave and the reception of its echo give a measure of the distance to the interface. Transmission ultrasound systems have been proposed, but these are currently in the experimental stage. Conventional ultrasound images are built up slice by slice in a manner analogous to CT (except that the slices are usually longitudinal rather than transverse); digital techniques are not needed to produce the images although almost all modern devices store the image in digital format to avoid electronic drift and to facilitate post processing. In this modality, the information associated with each voxel represents the strength of the echo at the corresponding point within the body; this in turn is a measure of acoustic impedance, a function of the type of materials present at the interface.

A major drawback of each of the imaging devices described above is that images are produced which comprise two dimensional slices of the internal anatomical structures being observed. Physicians must then mentally "stack" an entire series of these two dimensional slices in order to infer the structure of the three dimensional objects under investigation. Many problems are inherent in such an approach.

First, the interpretation of a series of stacked, two dimensional images by a physician requires a great deal of specialized knowledge and skill. Secondly, such an approach is extremely time consuming. Thirdly, the approach is prone to inaccuracy.

What is clearly needed is a medical display device which produces a three dimensional representation of internal anatomical structures produced from a full series of stacked two dimensional slices of that structure. Even more desirable is a medical image display device which provides the physician or other observer with the ability to manipulate the object and its image interactively in real time such that the object may be viewed from various directions and in various modes in real time. By real time display is meant that the video display output should be updated at or near video rates of 30 frames per second. Provided there is minimal or no delay between operator action and the corresponding change in the final image, this update rate would provide instantaneous perceptual feedback. It should be clear that such an interactive three dimensional display system permitting a physician to visualize and interact with a shaded three dimensional representation of an anatomical structure would greatly facilitate the examination of the structure in conjunction with medical research, clinical diagnoses, and the planning of surgical procedures.

A number of three dimensional display systems for medical objects have been described in the literature, but none of these provide realistic shaded images at the full resolution of the input data with real time interactive capabilities.

Three dimensional medical data sets can be displayed in the following ways: the data can be organized into a sequence of reprojected views or slices; it has been proposed to create true three dimensional images in space; and so-called two and a half dimensional (2.5D) images can be generated by projecting objects or object onto a two dimensional screen with depth cues given by shading.

Many computed tomography and magnetic resonance imaging display systems provide facilities to work through a sequence of two dimensional slices fairly rapidly, so that a trained physician can create a mental impression of the three dimensional structure. On the other hand, only the original slices captured by the imaging apparatus can be rapidly displayed. Reslicing or reformatting the image data to generate new two dimensional slices without re-imaging the patient, referred to as multi-planar reconstruction or MPR, slows the display process considerably.

True three dimensional images can be created in space using several different approaches. In one approach, a varifocal mirror is used to view slice images which are sequentially displayed on a cathode ray tube (CRT) under computer control. The mirror surface is vibrated in synchronism with the update of the CRT. Different images are seen as the mirror vibrates back and forth, giving a sense of depth. Another proposed approach employs a volume of a fluorescent gas, such as iodine-chlorine (I-Cl) vapor, which is excited to fluorscence by intersecting laser beams. The laser beams are scanned in a similar manner to the raster scanning of video monitors and television screens, except in a three dimensional sense.

The most familiar method of generating realistic images from a three dimensional scene is to project it onto a two dimensional screen and rely on motion parallax, projective geometry, shading, and hidden surface removal to create the illusion of depth. The result is similar to conventional television and motion pictures, which viewers readily intrepret as representing three dimensional scenes.

SUMMARY OF THE INVENTION

The present invention employs the last mentioned method of displaying three dimensional images on a two dimensional video display device and adds the step of displaying a slightly angularly displaced image on a second video display device for a true stereoscopic display of three dimensional image data. The two video display devices are positioned on a stereoscopic viewing unit, which is preferably supported on the head of the person viewing the images, to provide projection of the stereoscopic image components to the right and left eyes of the viewing person.

The system of the present invention comprises a pair of parallel image channels, one for the right stereoscopic image component and one for the left component. Each image channel includes a three dimensional display processor which reconstructs polygonal tomographic image data to form a three dimensional model of the anatomical structures of interest and selects the required data to display the structures represented by the image data from a selected viewpoint or perspective; a clipping and projection selector which selects the desired clip plane to eliminate data points on one side of the plane; a frame buffer or buffers for storing overlapping images; video display electronics including a color look-up table for selective shade control; and a video display device, such as a cathode ray tube. The operation of the 3D display processors is controlled and coordinated by a system computer to select display perspectives which are angularly displayed sufficiently for a stereoscopic impression to be created by the displayed image components. The system computer additionally derives polygon lists from image data in an image data storage medium or archive or directly from a tomographic imaging apparatus and forwards the polygon lists to the right and left image channels.

The tomographic imaging apparatus may be any of the currently practiced medical imaging techniques, such as x-ray computed tomography, magnetic resonance imaging, single photon emission computed tomography, positron emission tomography, or ultrasonic imaging. Since the system of the present invention is not generally an integral component of the imaging apparatus itself but merely processes image data derived by the imaging apparatus, the system of the present invention is applicable to any future imaging technique as long as the imaging data derived thereby is convertible to a format which can be used by the stereoscopic imaging system of the present invention.

The system computer of the stereoscopic imaging system includes a system memory, system mass storage devices and input devices, such as a keyboard and a screen location selection or pointing device such as a mouse or trackball. The system memory and mass storage devices store the operating software for the system computer and may also store the operating software for the 3D display processors.

The software preferably includes a polygon generator and interpolator of the type disclosed in U.S. Pat. No. 4,710,876 to Cline, et al. In this system, a polygon list is generated which represents a three dimensional cross-section of the tomographic image. The polygon list is then sent to a conventional three dimensional display processor where routines such as rotation, magnification, color selection, data range deletion, etc., are performed. In the present invention, two identical display processors are provided, one for the left display channel and one for the right display channel. Identical polygon lists are supplied to each display processor and a viewing angle is selected through the system computer. The left and right images are offset by an angle calculated to simulate left and right eye views and the display processors then use these viewing angles to construct simulated 3D stereoscopic images on left and right video displays.

Each display processor is a substantially conventional 3D image processor. Positional and normal vector information is received from the system computer. A viewing angle and viewing elevation are input as well as clipping information, shading control, etc. The resulting image is that of a 3 dimensional tomograph of a selected tissue type at the selected viewing angle. Hidden surfaces are removed via a conventional painter's algorithm. The display processors are synchronized via a common synchronizing signal derived from the master clock of the system computer. Such display processors are more particularly described in U.S. Pat. No. 4,719,585 granted Jan. 12, 1988 to Cline, et al., which is hereby incorporated by reference.

It is foreseen that the video display devices may be developed in the future which equal cathode ray tubes in resolution and color quality. For such video devices, the display processors would provide appropriate signal formats. At least one of the display processors has an output for a large video monitor external to the stereoscopic viewing unit for viewing by groups of practitioners.

OBJECTS OF THE INVENTION

The principal objects of the present invention are: to provide an improved medical imaging system; to provide such a system which significantly improves the ability of physicians to substantially noninvasively diagnose disease, anomalies, and injuries to internal organs and anatomical structures and to plan surgical procedures in relation thereto; to provide such a system which enhances the realism of medical images particularly with regard to relative location of components of the images; to provide such a system which provides a stereoscopic display of image data of anatomical structures obtained as data representing a plurality of tomographic or cross sectional type images of a patient; to provide such a system including a pair of three dimensional medical imaging type display processors to simultaneously process image data representing angularly displaced right and left stereoscopic components of a three dimensional image and display the stereoscopic components on corresponding right and left video display devices of a stereoscopic viewer; to provide such a system in which the right and left video display devices are mounted in a head worn harness; to provide such a system including a system computer to control and coordinate the right and left three dimensional display processors, derive polygon lists from image data in an image data storage medium or directly from a tomographic imaging apparatus and forward the polygon lists to the pair of display processors; to provide such a system which is capable of processing image data from a wide variety of tomographic imaging modalities including, but not limited to, x-ray computed tomography, magnetic resonance imaging, single photon emission computed tomography or gamma scintillation, positron emission tomography, and ultrasound imaging; to provide such a system which, with sufficient imaging apparatus and computer throughput, can process image data in substantially real time; and to provide such a stereoscopically displayed three dimensional medical imaging system which is economical to manufacture, precise in operation, and which is particularly well adapted for its intended purpose.

Other objects and advantages of this invention will become apparent from the following description taken in conjunction with the accompanying drawings wherein are set forth, by way of illustration and example, certain embodiments of this invention.

The drawings constitute a part of this specification and include exemplary embodiments of the present invention and illustrate various objects and features thereof.

DETAILED DESCRIPTION OF THE INVENTION

Figure 1:
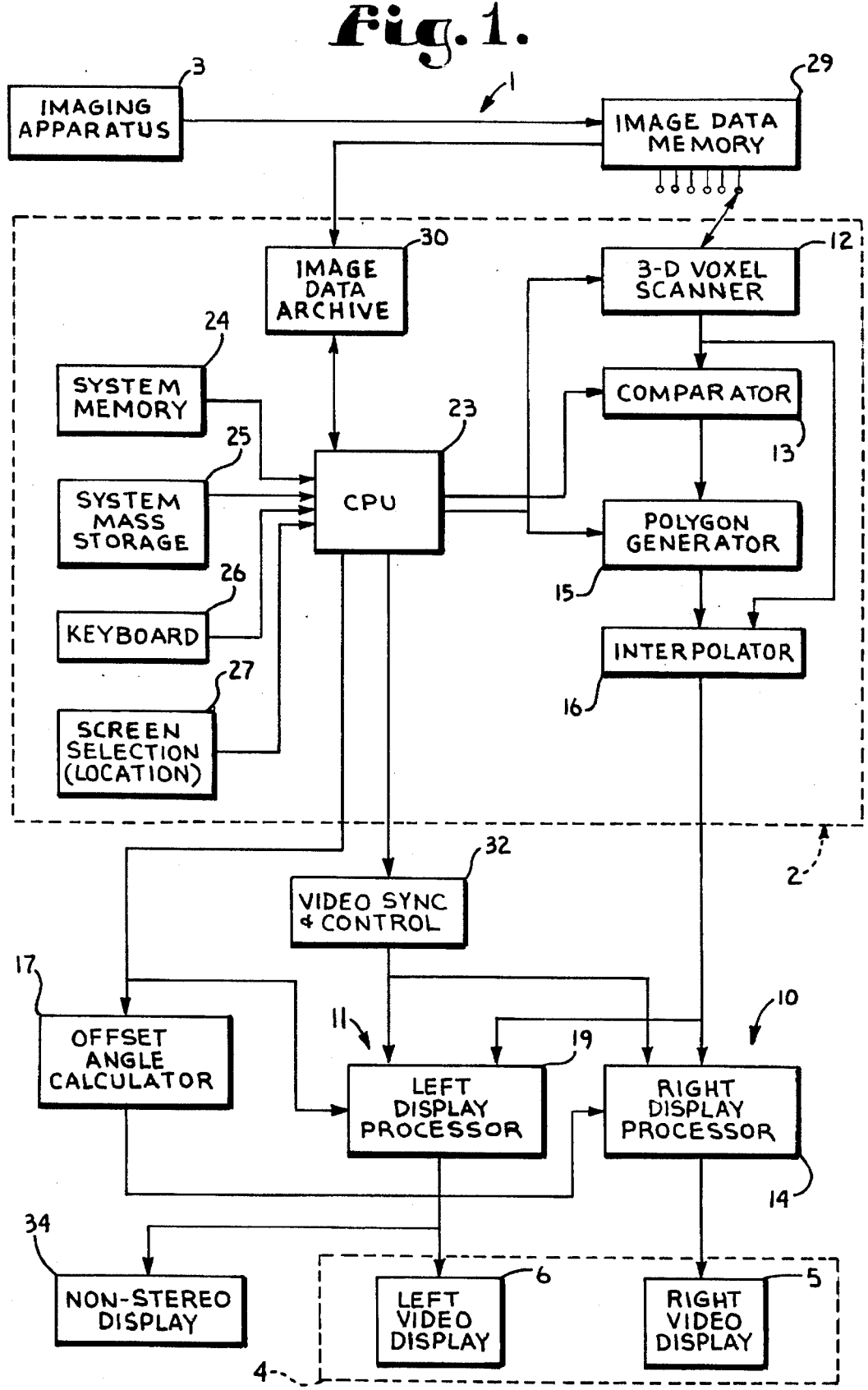
FIG. 1 is a block diagram illustrating the principal components of a stereoscopically displayed three dimensional medical imagining system embodying the present invention.

As required, detailed embodiments of the present invention are disclosed herein; however, it is to be understood that the disclosed embodiments are merely exemplary of the invention, which may be embodied in various forms. Therefore, specific structural and functional details disclosed herein are not to be interpreted as limiting, but merely as a basis for the claims and as a representative basis for teaching one skilled in the art to variously employ the present invention in virtually any appropriately detailed structure.

Referring to the drawings in more detail:

The reference numeral 1 generally designates a stereoscopically displayed three dimensional imaging system embodying the present invention. In general, the system 1 includes a stereoscopic three dimensional imaging system computer 2 which is interfaced between a tomographic imaging apparatus 3 and a stereoscopic viewing unit 4. The system 1 receives image data generated by the imaging apparatus 3, reconstructs the image data into a three dimensional model, generates right and left stereoscopic three dimensional image components of the model, and displays the stereoscopic components on right and left video display devices 5 and 6 of the stereoscopic display or viewing unit 4 for viewing.

The system 1 includes right and left image channels 10 and 11 interfaced between the system computer 2 and the video display devices 5 and 6 respectively. The right image channel includes a right three dimensional display processor and right video display device 5. Similarly, the left image channel 11 includes a left three dimensional display processor 19 and left video display device 6.

The system computer 2 includes CPU 23, system memory 24, system mass storage devices 25, a keyboard 26, and a screen location selection input 27. The mass storage devices 25 may include floppy disk drives and hard disk drives for storing an operating system and application programs for the system computer 2 and routines for manipulating the images displayed on the viewing unit 4 and for communicating with the imaging apparatus 3. The mass storage devices 25 may also store software for operating the 3D display processors 14 and 19. The keyboard 26 provides for command input to operate the system computer 2 to select image data sets to be displayed, for selecting image manipulation routines, and for required computer housekeeping activities. The screen location selection input or pointing device 27 may be a device such as a mouse, trackball, joystick, or the like for moving a cursor on the screens of the video display devices 5 and 6 to select areas of the displayed images to be manipulated or to select items from displayed menus for alternative command input.

The imaging apparatus 3 may be an implementation of any of a variety of tomographic imaging techniques as will be described in more detail below. The imaging apparatus 3 includes an image data memory 29 which stores data representing cross sectional images of a patient during operation of the apparatus 3. The image data is stored more or less permanently in a non-volatile image data archive medium 30 which may be a computer tape system, a write-once laser disc, or the like. The system 1 may be interfaced to the imaging apparatus 3 directly or to the image memory 29 and receive image data in real time during the imaging of a patient. Alternatively, the system 1 may be interfaced to the image data archive 30 and obtain image data therefrom at some time after the actual imaging process generates the data and at a location remote from the imaging apparatus 3.

Each of the three dimensional display processors 14 and 19 is similar to conventional monoscopic three dimensional medical display processors which are available from several manufacturers and which are in operation in a number of hospital facilities. Such computers are similar in many respects to computer systems used for flight simulators in their ability to represent and manipulate three dimensional scenes. In three dimensional medical imaging computers, data is reconstructed from a series of slice images or tomographs to form a three dimensional model of the slices in a stacked sequence. In some cases, it is necessary to average or interpolate between actual image data points to enhance the resolution of the displayed image.

As stated earlier, system computer 2 is preferably of the type disclosed in U.S. Pat. No. 4,710,876. In this type of imaging system, voxel scanner 12 selects a set of eight cubically adjacent data points for processing. These data points are supplied to a comparator 13 which is also supplied with a threshold value or range of values. The comparator then generates an 8 bit vector which is used to address a polygon generator 15 which may be a read only memory containing an edge connecting polygon list. The referenced patent utilizes triangles but it should be clear that any desired polygon shape could be used. An interpolator 16 then performs an interpolation operation on each of the voxel elements to generate a polygonal surface approximation to the selected surface as represented by the threshold. This polygon list is then supplied to the left and right display processors 19 and 14, respectively. The display processors then generate vectors or raster format signals which are supplied to left and right video displays 6 and 5. For a more detailed description of the imaging system, see the above referenced patent.

Figure 13:
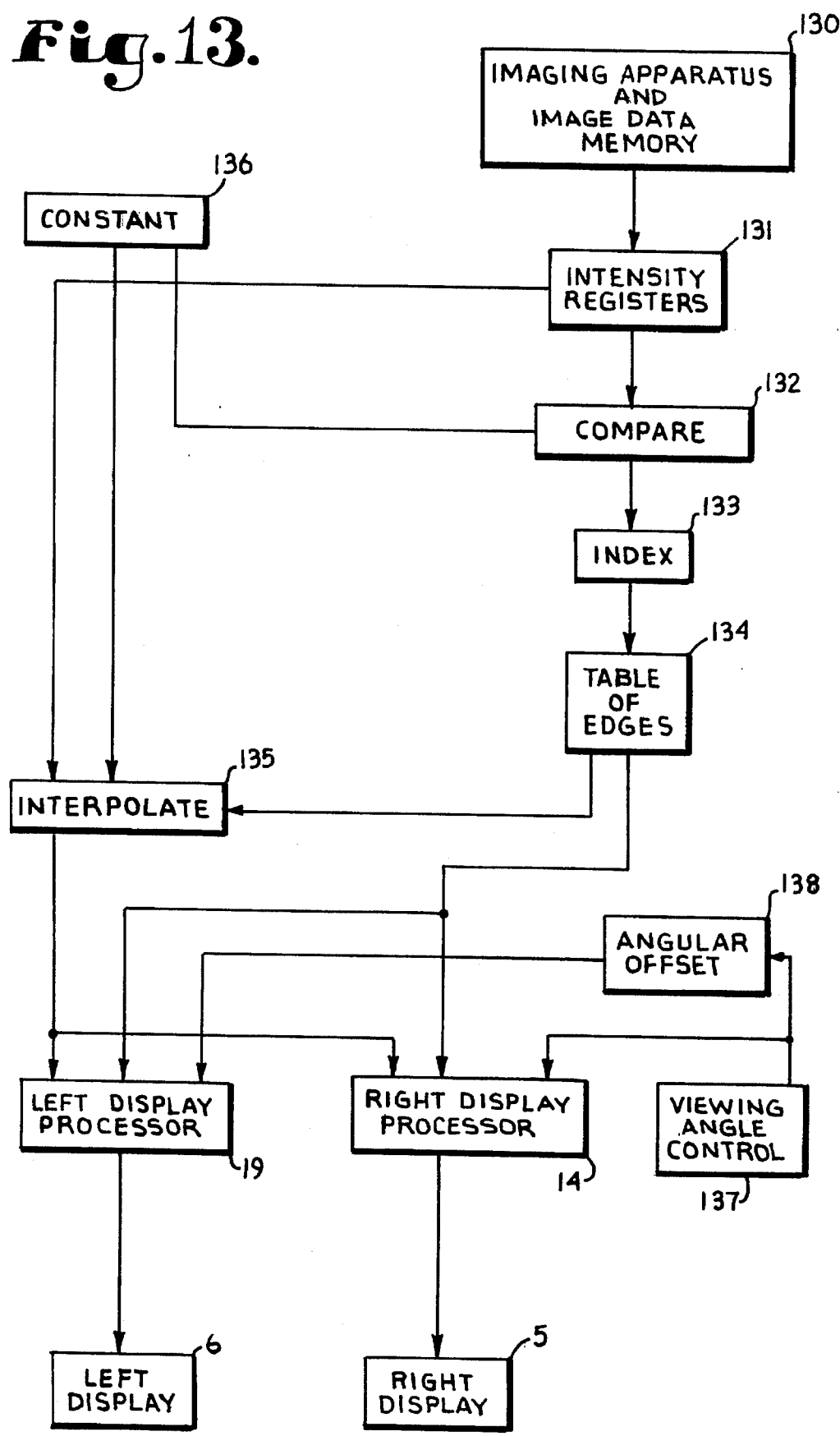
FIG. 13 is a flow chart illustrating data flow in the present invention.

A data flow diagram for the system is illustrated in FIG. 13. As explained in detail in the above referenced patent, voxel elements, each of which consists of 8 cubically adjacent data points, are loaded into intensity registers 131. These values are then compared with threshold values in comparison 132. The threshold values are constant with respect to each voxel. The comparison acts to generate an 8 bit vector which is used as an index to a table of edges at 133. An interpolation at block 134 is then performed utilizing the data from the edge table and the threshold and original voxel data to generate a polygon list representing a three dimensional tomograph. This list along with the data from the table of edges is then supplied to left and right display processors which generate vector or raster based 3 dimensional images. A control input from viewing angle and elevation control 137 is input to the processors, directly to one and offset by a calculated angle in the other to simulate a stereoscopic image. The angle is calculated to simulate an approximate 2 inch spacing between the eyes of an ordinary observer at a selected view elevation. This angle can be calculated geometrically or can be accessed via a look-up table of angles and elevations. This calculation can be performed by a separate angle generator 17 as shown in FIG. 1 or directly by CPU 23. Surface shading is added in the display processors, depending on the orientation of a surface, to add visual clues which give the appearance of three dimensionality to the image. Color hues and densities are often assigned to the image data depending on the relative value range of the data. Alternatively, color may be assigned according to the known colors or idealized colors of the organs and anatomical structures represented.

The above features of conventional monoscopic 3D display processors provide a static view of anatomical structures. Such computers are also usually provided with software routines to allow manipulation of the images, such as rotation of the displayed image, removal of portions of the displayed anatomical structures to reveal other details, removal of superfluous details or portions, magnification of a selected portion of the structures, and the like.

Each of the 3D display processors 14 and 19 is conventional. The operation of the computers 14 and 19 is coordinated by the system computer 2 such that the images generated thereby form right and left stereoscopic components of the same three dimensional model via viewing angle control and offset angle generator 17 in FIG. 1. Again, this angle simulates spacing between an observer's eyes. Additionally, when the images are manipulated, CPU 23 assures that such manipulations occur in coordination within the 3D display processors 14 and 19. For example, if the displayed anatomical structures are to be rotated, rotation must occur at the same rate and about the same axes on both display devices 5 and 6. The system computer 2 also synchronizes the displays 5 and 6 by providing a master clock signal which is converted by a video synchronizing circuit 32 to a synchronizing trigger signal such that the sweep circuitry in the displays are synchronized.

Figure 14:
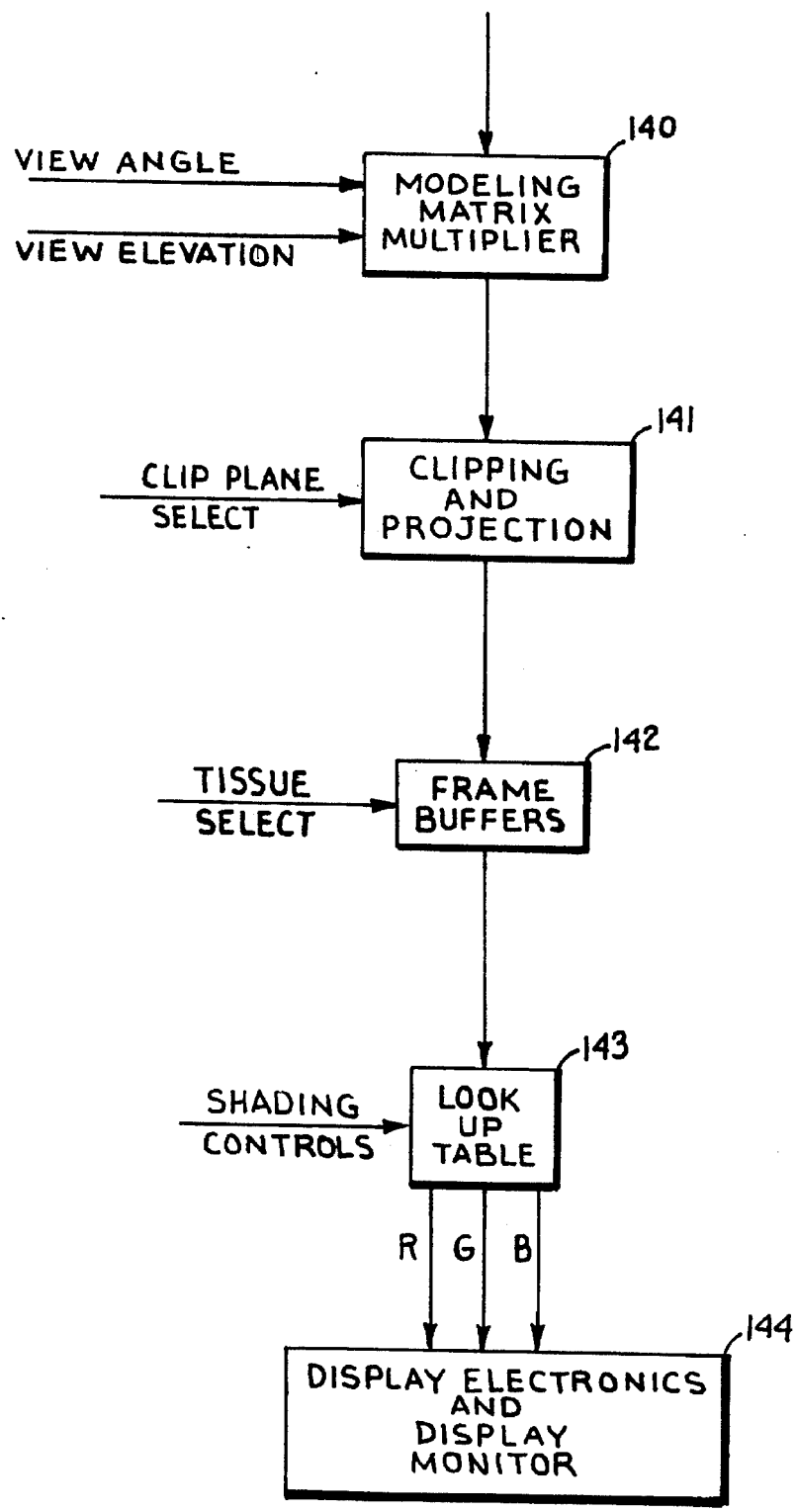
FIG. 14 is a block diagram illustrating the conventional principal components of one of the left and right display processors.

FIG. 14 illustrates a conventional display processor which could be utilized as the left and right display processors of the current invention. As earlier noted, such a processor is described in U.S. Pat. No. 4,719,585, to Cline, et al., which is hereby incorporated by reference. In FIG. 14, polygon list information is loaded from system computer 2 into modeling matrix multiplier 140. View angle and elevation are supplied via a matrix multiplation in block 140. A conventional clipping is selectively performed in block 141 to generate cross-section image data. Overlapping images are stored in frame buffer(s) 142 and shading control and hidden surface removal are performed via look up table 143. The overlapping images may, for example, represent bone structure, internal organs, and skin by selective use of different thresholds.

Preferably, at least one of the display processors, such as the left display processor 19, has an output for a nonstereoscopic display device 34. The display device 34 may, for example, be a large screen video monitor for monoscopically viewing of the images of the anatomical structures by a group of physicians or an assistant operating the system 1 at the direction of a physician viewing the images on the stereoscopic viewing unit 4.

FIGS. 2–6 diagrammatically illustrate a variety of types of imaging apparatus 3 which are capable of generating image data for processing by the stereoscopic three dimensional medical imaging system 1. In general, the imaging apparatus 3 causes energy to propagate through the patient. Parameters of the energy are altered as a result of interaction with the various anatomical structures within the patient, the energy alteration being measurable. The energy alterations are coordinated to location and assembled into image data representing an image of the patient by known algorithms. In some types of imaging apparatus 3, the image data can be directly displayed in real time. In others, the image data is stored as in a computer memory or other storage media for subsequent processing.

Figure 2:
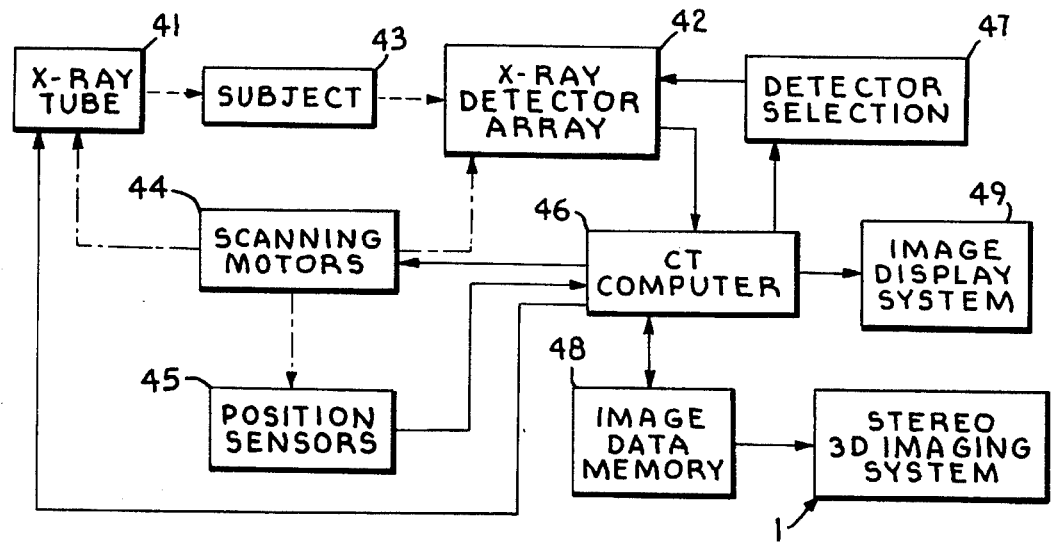
FIG. 2 is a simplified block diagram of a computed tomography system to derive image data for display on the three dimensional imaging system of the present invention.

FIG. 2 is a simplified illustration of x-ray computed tomography (CT) system 40. The CT system 40 includes an x-ray emitter or tube 41 which is mechanically connected to an x-ray detector or detector array 42 and moved in coordination therewith to irradiate a subject or patient 43. The detector array 42 includes a plurality of detector elements (not shown) which include essentially scintillation crystals in cooperation with photomultiplier tubes. The tube 41 and detector array 42 are positioned by an arrangement of scanning motors 44 to scan the subject 43 in a particular manner, such as in a circumferential pattern about an axis passing through the subject and translated along the axis. At each axial position, the translational movement is halted to generate image date representing a cross sectional or slice image of the patient. Position sensors 45 detect the position of the tube 41 and array 42, or alternatively detect the position of members of the scanning motors 44.

The scanning process is controlled by a CT computer 46 which also receives signals representing time and position dependent data representing the changes in the x-ray beams, or absorption thereof, as a result of interaction with the patient 43. In some CT systems 40, the x-ray tube 41 and detector array 42 are not always moved in unison. Instead, the detector array 42 is held fixed in some positions while the tube 41 is moved. In such cases, individual detector elements or groups of detector elements are selected or activated by the CT computer 46 through detector selection circuitry 47. Additionally, the CT computer 46 controls the activation of the x-ray tube 41 to minimize patient irradiation.

The signals from the detector array 42 are converted from an analog format to digital representations thereof and stored by the computer 46 in an image data memory 48. Concurrently or at a later time, the image data is converted to video signals and displayed on an image display system 49. As illustrated, the stereoscopic three dimensional system 1 may be interfaced to the image data memory 48 to receive image data therefrom. Alternatively, the system 1 may be interfaced directly to the CT computer 46 or to a nonvolatile image data archive, such as the archive 30, which is interfaced to the CT computer 46.

Figure 3:
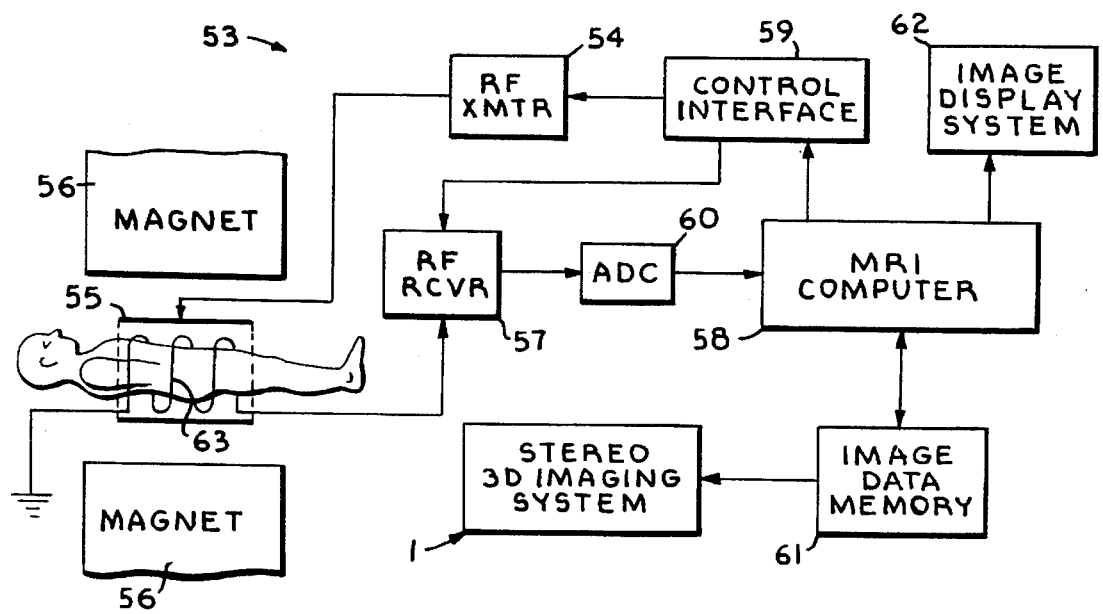
FIG. 3 is a simplified block diagram of a magnetic resonance imaging system to derive image data for display on the three dimensional imaging system of the present invention.

FIG. 3 diagrammatically illustrates a simplified magnetic resonance imaging (MRI) system 53. MRI systems exploit the magnetic activity of the nuclei of atoms of certain elements at characteric radio frequencies, known as their Larmor frequency. In medical imaging using these techniques, the principal element of interest is hydrogen due to its presence in water in body tissues. In nuclear magnetic resonance (NMR) techniques, employed in magnetic resonance imaging, the nuclei are excited by radio frequency signals generated by a radio frequency transmitter 54 through a system of transmitter coils 55 in the presence of a magnetic field provided by a large magnet 56, which is often a superconducting magnet. The relaxation activity of the nuclei is detected by a radio frequency receiver 57 by means of a system of receiving coils 63 positioned within the magnet 56.

The operation of the transmitter 54 and receiver 57 is controlled and coordinated by an MRI computer 58 through a control interface 59. The parameters measured by the MRI system 53 may relate to resonant nuclei density or to characteristic relaxation times known as T1 and T2. The patient is scanned by signals applied to gradient coils (not shown) under control of the MRI computer 58 which steer the excitation energy from the transmitter coils 55. Signals representing values of these parameters are converted from analog to digital representations by an analog to digital converter (ADC) 60 for processing by the MRI computer 58. The computer 58 processes the digital signals to derive image data representing an image of a slice through the patient, in much the same form as image data derived by the CT system 40. The image data is stored in an image data memory 61 and displayed by an image display system 62. The image data stored in the 61 may be retrieved by the stereoscopic imaging system 1 for stereoscopic display thereon.

Figure 4:
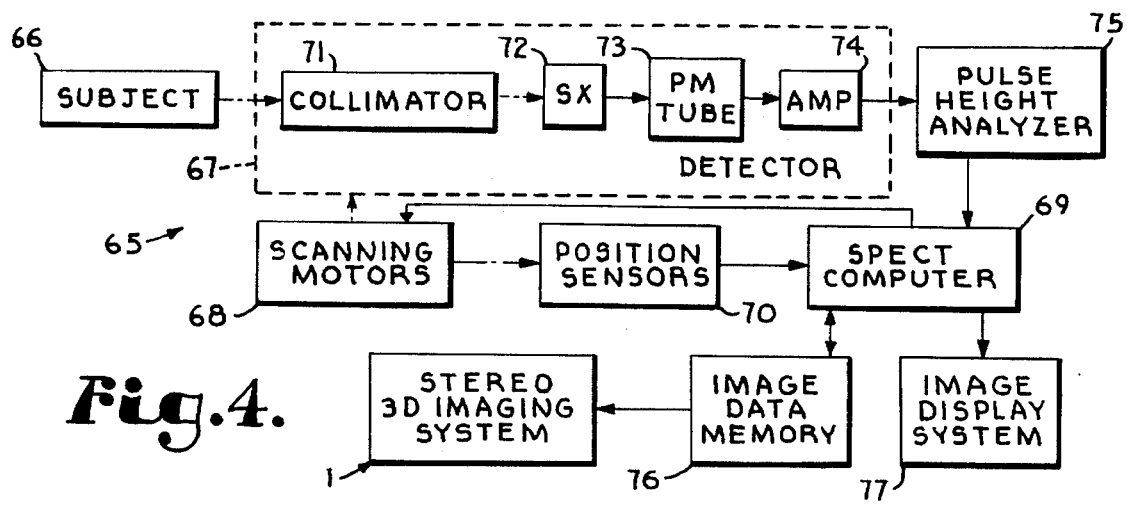
FIG. 4 is a simplified block diagram of a single photon emission computed tomography system to derive image data for display on the three dimensional imaging system of the present invention.

FIG. 4 is a simplified illustration of a single photon emission computed tomography (SPECT) system 65. ASPECT system 65 or tomographic gamma scintillation system is similar in many respects to the x-ray CT system 40, the differences consisting mainly in the source and characteristics of the energy propagated through the subject or patient 66. In a SPECT system 65, a gamma emitting radiopharmaceutical is administered to the subject 66. The radiopharmaceutical concentrates into certain organs and tissues, depending on the type employed. Gamma photons emanating from the radiopharmaceutical are detected by a detector assembly 67 which is scanned about the subject 66 by scanning motors 68 under the control of a SPECT computer 69 via position sensors 70.

A typical detector assembly 67 includes a collimator 71, a scintillation crystal (SX) 72, a photomultiplier (PM) tube 73, and a preamplifier or amplifier 74. The collimator 71 discriminates gamma photons on the basis of direction to thereby focus the detector assembly 67 and exclude scattered gamma photons. The scintillation crystal 72 absorbs gamma photons and emits visible light photons which cause the release of electrons in the photomultiplier tube 73 by the photoelectric effect. The PM tube 73 multiplies this effect to form an electrical signal which is amplified by the preamplifier 74. The signal from the amplifier 74 is processed by a pulse height analyzer 75 which is an amplitude discriminating device. Only signals having with amplitudes falling in a selected range are passed. Those that are passed are analog to digital converted by a converter within the SPECT computer 69. The converted signals are transformed into image data by the SPECT computer 69 which is stored in the image data memory 76, displayed on the image display system 77, and made available to the stereoscopic three dimensional imaging system 1.

Figure 5:
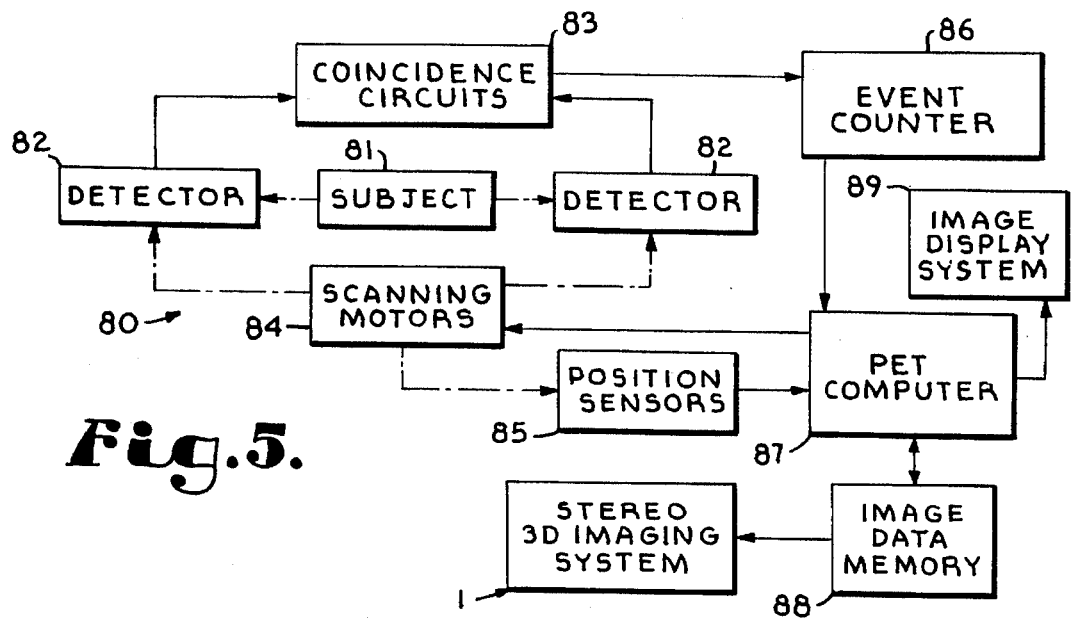
FIG. 5 is a simplified block diagram of a positron emission tomography system to derive image data for display on the three dimensional imaging system of the present invention.

FIG. 5 diagrammatically illustrates a positron emission tomography (PET) system 80. In PET systems, positron emitting radiopharmaceuticals are administered to the subject or patient 81. The positrons collide with surrounding matter within the subject and at low kinetic energies are captured by electrons. An annihilation process of a positron and electron results in the emission of two 511 keV photons at an angle of 180 degrees relative to one another. A pair of detectors 82 on opposite sides of the subject 81 detect the two photons simultaneously which is determined by coincidence circuits 83. The detectors are similar in many respects to the type of detector assembly 67 used in the SPECT system 65. The detectors 82 are scanned by scanning motors 84, the scanning being sensed by position sensors 85. The principal parameter measured by PET systems is a counting of detected coincidences by an event counter circuit 86. This count in relation to the position of the detectors 82 can be reconstructed into data representing an slice image by a PET computer 87 in much the same manner as the absorption of x-rays in the CT system 40 is converted into image data. The image data is stored in an image data memory 88, displayed on an image display system 89, and made available to the system 1 for reconstruction into a three dimensional model for stereoscopic display thereon.

Figure 6:
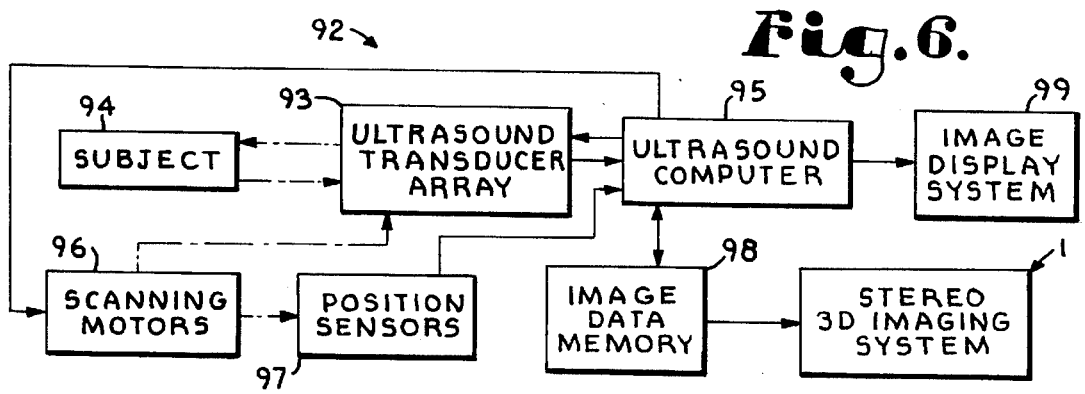
FIG. 6 is a simplified block diagram of an ultrasound system to derive image data for display on the three dimensional imaging system of the present invention.

FIG. 6 diagrammatically illustrates an ultrasound imaging system 92 including an ultrasound transducer array 93 which is positioned on the skin of a patient or subject 94. Elements of the array 93 are alternately activated as transmitters and receivers by an ultrasound computer 95. The sound energy emitter by the array 93, which may have a frequency range of one to ten megahertz, is propagated through the tissues and anatomical structures of the subject 94 and reflected back to the array 93 and received thereby. The amplitudes of the echoes are related to the acoustic impedances encountered at the interfaces between various anatomical structures. The propagation time is related to the distance travelled by the ultrasound pulses.

In conventional ultrasound imaging systems using linear arrays of transducer elements, the sound beam is steered by various mechanical or electrical means to cover and thereby image a fan shaped sector of the subject. As long as the array is held in a fixed position, a single slice image is produced. It has been proposed to produce and store image data representing a series of sequential slices, in much the same manner as a series of CT slices are produced.

In the illustrated ultrasound system 92, the transducer array 93 is positioned by scanning motors 96 under the control of the ultrasound computer 95, the position of the array 93 or components of the motors 96 being indicated by position sensors 97. The received output of the transducer array 93 and position signals from the position sensors 97 are fed to the computer 95 for organizing image data representing a series of image slices of the subject 94. The image data is stored in an image data memory 98, displayed on an image display system 99, and made available for reconstruction into a three dimensional model of a segment of the subject 94 and display thereof on the stereoscopic three dimensional imaging system 1.

Figure 7:
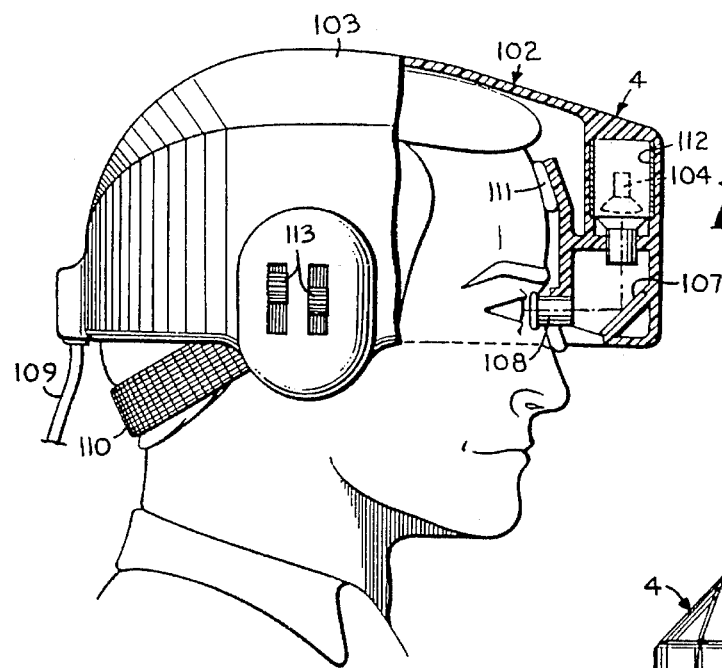
FIG. 7 is a side elevational view of a first stereoscopic display unit of the imaging system employing miniature cathode ray tubes as video display devices, with portions broken away to illustrate the optical elements which project a pair of images into the eyes of the viewer.
Figure 8:
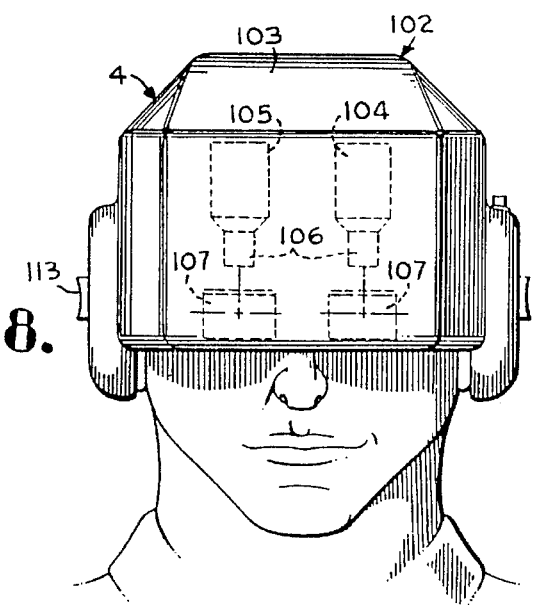
FIG. 8 is a front elevational view of the first display unit of the imaging system.
Figure 9:
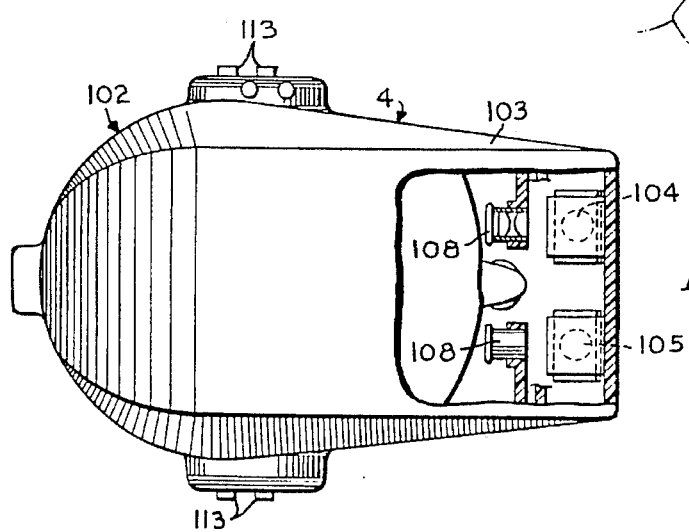
FIG. 9 is a top plan view of the first display unit with portions broken away to illustrate further details of the projection optics.

FIGS. 7–9 illustrate a first embodiment 102 of a head worn stereoscopic viewing or display unit 4. The unit 102 includes a cap or helmet 103 in which the components of the unit 102 are mounted. The right and left video display devices 5 and 6 are miniature color cathode ray tubes (CRT's) 104 and 105 respectively which are mounted within the helmet 103 for indirect projection of the images therefrom into the eyes of a person viewing the displays in order to decrease the possibility of projecting x-rays from the CRT's 104 and 105 into the eyes of the viewer.

The CRT's 104 and 105 are mounted for downward projection of the images thereof through projection optical elements 106 toward right angle reflecting elements 107 such as mirrors or prisms and from there through viewing lenses 108 to the eyes of the viewer. The viewing lenses 108 are provided to compensate for the short focal distance between the eyes of the viewer and the display devices 104 and 105 such that the images can be focused at a greater effective distance. The viewing lenses 108 are preferably finely adjustable to accommodate the visual capabilities of the eyes of the viewer. Further, the lateral positions of the right and left video display components are preferably adjustable to accommodate the spacing between the eyes of the viewer, although such adjustment means are not illustrated.

The video signals from the display electronics are provided to the components within the helmet 103 by a cable 109 which enters the unit 102 at the rear of the helmet 103. The helmet 103 preferably includes an adjustable harness for fitting the helmet to the head of the viewer, as represented by an elastic band 110. A forehead pad 111 is provided to maintain the position of the optical elements of the unit 102 in relation to the eyes fo the viewer. X-ray shields 112 are positioned to enclose the CRT's 104 and 105. The helmet 103 may be provided with controls 113 for adjusting characteristics of the images displayed on the CRT's, such as brightness and contrast.

Figure 10:
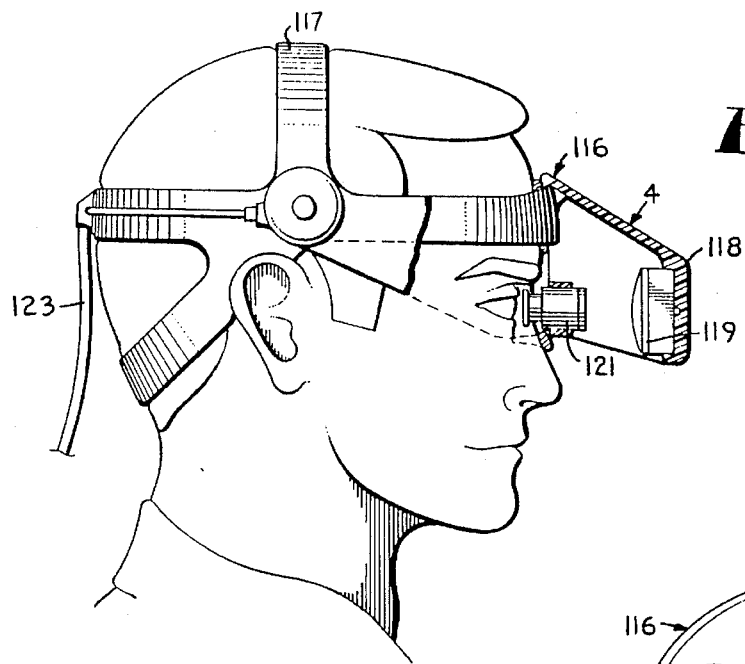
FIG. 10 is a side elevational view of a second stereoscopic display unit employing liquid crystal devices, with a portion broken away to illustrate details of the second display unit.
Figure 11:
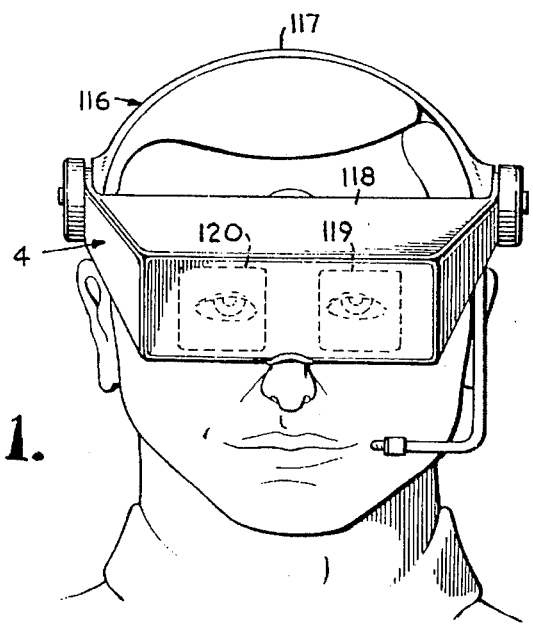
FIG. 11 is a front elevational view of the second display unit.
Figure 12:
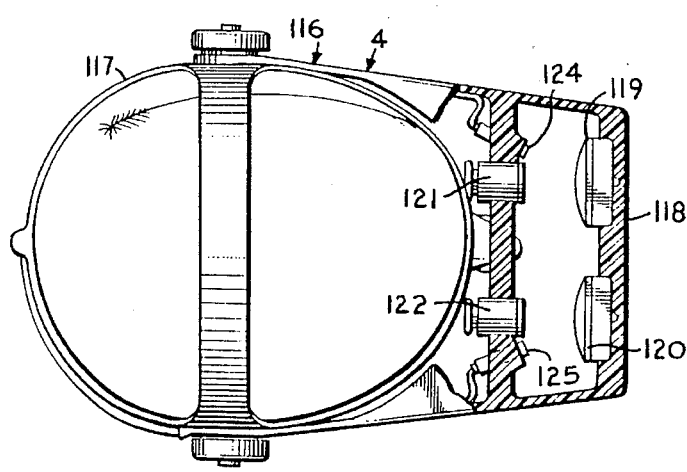
FIG. 12 is a top plan view of the second display unit with a portion broken away to illustrate internal details thereof.

FIGS. 10–12 illustrate a second embodiment 116 of the stereoscopic viewing unit 4. The unit 116 generally includes a support harness or headband 117 to which is pivotally connected a visor 118 having right and left video display devices 119 and 120 positioned therein. The harness 117 is preferably adjustable and is adapted for wearing on the head of a medical practitioner who is viewing the images generated by the system 1. In addition to the display devices 119 and 120, the visor 118 provides a mounting for right and left optical elements 121 and 122 which compensate for the close spacing between the video display devices 119 and 120 and the eyes of the viewer.

The illustrated right and left video display devices 5 and 6 are color dot matrix type liquid crystal displays (LCD's) 119 and 120. LCD's are much lighter in weight than cathode ray tubes, but their image resolution and color quality is currently not quite as good as comparably sized CRT's. LCD's are low voltage devices; thus, there is no problem of x-ray emissions therefrom. As a result, the LCD's 119 and 120 are mounted directly in line of sight of the eyes of the viewer. This results in a reduction in weight of the viewing unit 116 since mirrors or prisms are not required for reflecting the images.

It is desirable to mount a major portion of the display electronics, such as synchronization and sweep control circuitry elsewhere than directly on the viewing unit 116 to keep the unit as light as possible. The display electronics are preferably mounted on a belt (not shown) worn by the practitioner such that the video signals are conducted to the display devices 119 and 120 by cables 123. The LCD's 119 and 120 do not radiate their own light and must be illuminated by separate sources. As illustrated, right and left light sources 124 and 125 are positioned within the unit 116 to illuminate the LCD's 119 and 120. Alternatively, backlight sources (not shown) may be provided behind the LCD's 119 and 120.

Although the head worn stereoscopic display units 102 or 116 are preferred, the stereoscopic viewing unit 4 may alternatively be adapted as a free standing unit (not shown). Such a free standing unit would be designed along the same lines as the units 102 and 116 with less concern for weight.

It is to be understood that while certain forms of the present invention have been illustrated and described herein, it is not to be limited to the specific forms or arrangement of parts described and shown.

What is claimed and desired to be secured by Letters Patent is as follows:

1. A method of three dimensionally imaging and stereoscopically displaying images of anatomical structures within an organism comprising the steps of:

(a) providing an energy having a selected parameter;
    (b) propagating said energy within an organism having anatomical structures therein such that said energy interacts with said anatomical structures;
    (c) receiving said energy after said interaction with said anatomical structures;
    (d) measuring changes in said selected parameter of said energy as a result of interaction with said anatomical structures;
    (e) converting said changes to image data representing images of said anatomical structures;
    (f) performing said propagating, receiving, measuring, and converting steps in such a manner as to obtain said image data in a form of a plurality of closely spaced and sequential two dimensional arrays of spatially related image data points having values related to said change in said selected parameter of said energy, said arrays forming cross sectional images of a segment of said organism;
    (g) assembling said image data in such a manner as to form a three dimensional model;
    (h) transforming said three dimensional model into independent, angularly displaced right and left three dimensional video signals representing right and left eye three dimensional stereoscopic components of said three dimensional model from a first perspective, said transforming step including the steps of creating a three dimensional view from said first perspective of said three dimensional image data, said first perspective representing one of said right or left eye stereoscopic components and rotating said three dimensional image data from said first perspective to a second perspective and creating a second three dimensional view from said second perspective, said second perspective representing the other of said left and right eye stereoscopic components;
    (i) providing a stereoscopic display unit including separate, independent right and left video displays;
    (j) displaying said right three dimensional model stereoscopic image component of a three dimensional image of said three dimensional model on said right video display; and
    (k) displaying said angularly displaced left three dimensional model stereoscopic image component of said three dimensional image of said three dimensional model on said left video display.

2. A method as set forth in claim 1 including the steps of:

(a) positioning said right and left video display devices in a head worn viewing harness in which said right and left video display devices are supported by the head of a person viewing said images.

3. A method as set forth in claim 1 and further including the steps of:

(a) causing said image of said anatomical structures as displayed to rotate about an axis from said first perspective to a third perspective; and
    (b) repeating said transforming step with said third perspective representing said one of said right or left eye views.

4. A method as set forth in claim 1 including the steps of:

(a) correlating said range of shades of display color to a range of changes in said selected parameter of said energy as a result of interaction with said anatomical structures;
    (b) selecting an inhibition range of said shades of display color; and
    (c) causing the inhibition of the display of the inhibition range of said shades of display color to thereby enhance the view of remaining portions of said image.

5. A method as set forth in claim 1 wherein said converting step includes:

(a) interpolating to provide average image data point values between adjacent image data points to derive averaged image points interspersed among said data image points.

6. A method as set forth in claim 1 including the steps of:

(a) storing said image data;
    (b) recalling said image data at a time remote from said generating step; and
    (c) performing said transforming and displaying steps on said recalled image data.

7. A method as set forth in claim 1 including:

(a) performing said generating, propagating, receiving, and measuring steps using an x-ray computed tomography imaging apparatus.

8. A method as set forth in claim 1 including:

(a) performing said generating, propagating, receiving, and measuring steps using a magnetic resonance imaging apparatus.

9. A method as set forth in claim 1 including:
(a) performing said generating, propagating, receiving, and measuring steps using a positron emission tomography imaging apparatus.

10. A method as set forth in claim 1 including:
(a) performing said generating, propagating, receiving, and measuring steps using a single photon emission computed tomography imaging apparatus.

11. A method as set forth in claim 1 including:
(a) performing said generating, propagating, receiving, and measuring steps using a ultrasound imaging apparatus.

12. An apparatus for stereoscopically imaging anatomical structures comprising:
(a) imaging means deriving image data representing changes in a selected parameter resulting from interaction of an energy with anatomical structures of a segment of an organism upon the propagation of said energy within said organism;
(b) image data storage means interfaced with said imaging means and storing said image data;
(c) computer means interfaced with said image data storage means for receiving said image data, assembling said image data in such a manner as to form a three dimensional model of said segment of said organism, generating independent right and left eye angularly displaced three dimensional stereoscopic image data representing respective right and left stereoscopic component images of said three dimensional model by rotating said three dimensional model to yield respective right and left eye perspective components from a selected perspective view of said three dimensional model; and
(d) stereoscopic display means interfaced with said computer means and including separate, independent right and left video displays, said display means receiving said right and left three dimensional model stereoscopic image data and transforming same into right and left video signals which are applied respectively to said right and left video displays to display said right and left stereoscopic component images respectively thereon.

13. An apparatus as set forth in claim 12 including:
(a) a viewing harness supporting said right and left video display devices on the head of a person viewing said images.

14. An apparatus as set forth in claim 12 wherein said computer means further includes:
(a) a system computer connected to said image data storage means and to said right and left three dimensional display processors, said system computer providing said processors with three dimensional model image data derived from said image data storage means, said system computer also coordinating the operation of said right and left three dimensional computers to display respective right and left stereoscopic image components of said three dimensional model.

15. An apparatus as set forth in claim 12 wherein:
(a) said computer means includes means for selectively causing said image of said anatomical structures as displayed to rotate about an axis to allow viewing said image from a different perspective.

16. An apparatus as set forth in claim 12 wherein said computer means includes:
(a) means for correlating said range of shades of display color to a range of changes in said selected parameter of said energy as a result of interaction with said anatomical structures;
(b) means for selecting an inhibition range of said shades of display color; and
(c) means for selectively inhibiting the display of the inhibition range of said shades of display color to thereby enhance the view of remaining portions of said image.

17. An apparatus as set forth in claim 12 wherein:
(a) said imaging means propagates said energy within said organism and receives said energy in such a manner as to obtain said image data as an array of spatially related image data points having values related to said changes in said selected parameter; and
(b) said computer means is programmed to:
(1) interpolate to provide average image data point values between adjacent image data points interspersed among said image data points.

18. An apparatus as set forth in claim 12 wherein:
(a) said imaging means propagates said energy within said organism and receives said energy in such a manner as to obtain said image data in a form of a plurality of closely spaced and sequential two dimensional cross sectional images of a segment said organism; and
(b) said computer means is programmed to:
(1) assemble said image data in such a manner as to form said three dimensional model of said segment of said organism.

19. An apparatus as set forth in claim 12 wherein:
(a) said imaging means includes scanned energy detector means to receive said energy propagated within said organism in such a manner as to obtain said image data in a form of a plurality of closely spaced and sequential two dimensional arrays of spatially related image data points having values related to said changes in said selected parameter of said energy, said arrays forming cross sectional images of a segment of said organism.

20. An apparatus as set forth in claim 12 wherein said imaging means includes:
(a) an x-ray computed tomography imaging system.

21. An apparatus as set forth in claim 12 wherein said imaging means includes:
(a) a magnetic resonance imaging system.

22. An apparatus as set forth in claim 12 wherein said imaging means includes:
(a) a positron emission tomography imaging system.

23. An apparatus as set forth in claim 12 wherein said imaging means includes:
(a) a single photon emission computed tomography imaging system.

24. An apparatus as set forth in claim 12 wherein said imaging means includes:
(a) an ultrasound imaging system.

25. An apparatus for stereoscopically imaging anatomical structures comprising:
(a) imaging means deriving image data representing changes in a selected parameter resulting from interaction of an energy with anatomical structures of a segment of an organism upon the propagation of said energy within said organism, said image data being in a form of a plurality of closely spaced and sequential two dimensional arrays of spatially related image data points having values related to said changes in said selected parameter of said energy, said arrays forming cross sectional images of a segment of said organism;

(b) image data storage means interfaced with said imaging means and storing said image data;

(c) computer means interfaced with said image data storage means for receiving said image data, assembling said image data in such a manner as to form a three dimensional model of said segment of the organism and generating independent right and left eye angularly displaced three dimensional stereoscopic image data representing respective right and left three dimensional stereoscopic component images of said anatomical structures by rotating said three dimensional model to yield respective right and left eye perspective components from a selected perspective view of said three dimensional model;

(d) stereoscopic display means interfaced with said computer means and including separate, independent right and left video displays, said display means receiving said right and left stereoscopic image data and transforming same into right and left video signals which which represent said right and left stereoscopic component images, respectively;

(e) a right three dimensional model stereoscopic image component of a three dimensional image of said three dimensional model being displayed on said right video display; and (f) an angularly displaced left three dimensional model stereoscopic image component of said three dimensional image of said three dimensional model being displayed on said left video display.

26. An apparatus as set forth in claim 25 including:

(a) a viewing harness supporting said right and left video display devices on the head of a person viewing said images.

27. An apparatus as set forth in claim 25 wherein:

(a) said computer means includes a right and a left three dimensional display processor;

(b) said right and left three dimensional display processors each receive said processed image data and selected viewing elevations and angles, said right and left display processors including means for rotating said image data in such a manner as to form said angularly displaced right and left three dimensional models of said segment of said organism, and communicating to said display means said respective right and left models as stereoscopic image components of said three dimensional model.

28. An apparatus as set forth in claim 27 wherein said computer means further includes:

(a) a system computer connected between said image data storage means and said right and left three dimensional display processors and providing said processors with processed image data from said image data storage means and said viewing elevations and angles, said system computers also coordinating the operation of said right and left three dimensional display processors to display said right and left stereoscopic image components of said three dimensional model.

29. An apparatus as set forth in claim 25 wherein:

(a) said computer means includes means for selectively causing said three dimensional model of said anatomical structures as displayed to rotate about an axis to change said selected perspective to a different angle.

30. An apparatus as set forth in claim 25 wherein said computer means includes:

(a) means for correlating said range of shades of display color to a range of changes in said selected parameter of said energy as a result of interaction with said anatomical structures;

(b) means for selecting an inhibition range of said shades of display color; and (c) means for selectively inhibiting the display of the inhibition range of said shades of display color to thereby enhance the view of remaining portions of said image.

31. An apparatus as set forth in claim 25 wherein said computer means includes:

(a) means for interpolating to provide average image data point values between adjacent image data points of said image data to derive averaged image points interspersed among said image data points.

32. An apparatus as set forth in claim 25 wherein said imaging means includes:

(a) an x-ray computed tomography imaging system.

33. An apparatus as set forth in claim 25 wherein said imaging means includes:

(a) a magnetic resonance imaging system.

34. An apparatus as set forth in claim 25 wherein said imaging means includes:

(a) a positron emission tomography imaging system.

35. An apparatus as set forth in claim 25 wherein said imaging means includes:

(a) a single photon emission computed tomography imaging system.

36. An apparatus as set forth in claim 25 wherein said imaging means includes:

(a) an ultrasound imaging system.

* * * * *